United States Patent
Boussarie et al.

(10) Patent No.: US 11,912,640 B2
(45) Date of Patent: Feb. 27, 2024

(54) PROCESS FOR PURIFYING 1-CHLORO-3,3,3-TRIFLUOROPROPENE

(71) Applicant: ARKEMA FRANCE, Colombes (FR)

(72) Inventors: Emmanuel Boussarie, Pierre-Benite (FR); Kevin Hisler, Pierre-Benite (FR); Anne Pigamo, Pierre-Benite (FR)

(73) Assignee: Arkema France, Colombes (FR)

( * ) Notice: Subject to any disclaimer, the term of this patent is extended or adjusted under 35 U.S.C. 154(b) by 213 days.

(21) Appl. No.: 17/600,200

(22) PCT Filed: Apr. 1, 2020

(86) PCT No.: PCT/EP2020/059233
§ 371 (c)(1),
(2) Date: Sep. 30, 2021

(87) PCT Pub. No.: WO2020/201342
PCT Pub. Date: Oct. 8, 2020

(65) Prior Publication Data
US 2022/0204428 A1    Jun. 30, 2022

(30) Foreign Application Priority Data
Apr. 3, 2019   (FR) ...................................... 1903539

(51) Int. Cl.
*C07C 17/20* (2006.01)
*C07C 17/395* (2006.01)

(52) U.S. Cl.
CPC .......... *C07C 17/206* (2013.01); *C07C 17/395* (2013.01)

(58) Field of Classification Search
CPC ..... C07C 17/206; C07C 17/395; C07C 17/25; C07C 17/38; C07C 21/18
See application file for complete search history.

(56) References Cited

U.S. PATENT DOCUMENTS

| | | | |
|---|---|---|---|
| 6,166,274 A | 12/2000 | Chen et al. | |
| 2014/0275662 A1 | 9/2014 | Haluk et al. | |
| 2015/0203424 A1 | 7/2015 | Okamoto et al. | |
| 2017/0253543 A1* | 9/2017 | Sharratt | B01J 23/90 |
| 2018/0346396 A1 | 12/2018 | Pigamo et al. | |
| 2019/0031583 A1* | 1/2019 | Okamoto | B01J 27/08 |

FOREIGN PATENT DOCUMENTS

| | | |
|---|---|---|
| JP | 2016160233 A | 9/2016 |
| WO | 0181353 A1 | 11/2001 |
| WO | 2014010530 A1 | 1/2014 |
| WO | 2014099464 A1 | 6/2014 |
| WO | 2014189674 A1 | 11/2014 |
| WO | 2015104517 A1 | 7/2015 |
| WO | 2015167784 A1 | 11/2015 |
| WO | 2016148957 A1 | 9/2016 |
| WO | 2017031406 A1 | 2/2017 |
| WO | 2017050686 A1 | 3/2017 |

OTHER PUBLICATIONS

ISA/EP; International Search Report and Written Opinion for International Patent Application No. PCT/EP2020/059233 dated Sep. 4, 2020, 19 pages.

* cited by examiner

Primary Examiner — Jafar F Parsa
(74) Attorney, Agent, or Firm — NK Patent Law

(57) ABSTRACT

The present invention relates to a process for neutralizing a composition A comprising 1-chloro-3,3,3-trifluoropropene, 1,1-dichloro-1,3,3-trifluoropropane and one or more acid compound(s) of formula HX with X=F or Cl; said process comprising the step a) of bringing said composition A into contact with a solution B under conditions capable of limiting the formation of 1-chloro-1,3,3-trifluoropropene.

14 Claims, No Drawings

PROCESS FOR PURIFYING 1-CHLORO-3,3,3-TRIFLUOROPROPENE

CROSS-REFERENCE TO RELATED APPLICATIONS

This application is a U.S. National Stage application of International Patent Application No. PCT/EP2020/059233, filed on Apr. 1, 2020, which claims the benefit of French Patent Application No. FR1903539, filed on Apr. 3, 2019.

TECHNICAL FIELD OF THE INVENTION

The present invention relates to a process for the purification of hydrochlorofluoroolefins. In particular, the present invention relates to a process for purifying 1-chloro-3,3,3-trifluoropropene. The present invention also relates to a process for producing 1-chloro-3,3,3-trifluoropropene.

TECHNOLOGICAL BACKGROUND OF THE INVENTION 3,3,3-Trifluoro-1-chloropropene, or alternatively 1-chloro-3,3,3-trifluoropropene (HCFO-1233zd), exists in the form of two isomers: the cis isomer, namely Z-3,3,3-trifluoro-1-chloropropene (HCFO-1233zdZ), and the trans isomer, namely E-3,3,3-trifluoro-1-chloropropene (HCFO-1233zdE). They have different boiling points of, respectively, 18.5° C. for the trans compound and 39.5° C. for the cis compound.

Fluids based on E-3,3,3-trifluoro-1-chloropropene (HCFO-1233zdE) have found numerous applications in varied industrial fields, in particular as heat transfer fluids, propellants, foaming agents, blowing agents, gaseous dielectrics, monomers or polymerization media, support fluids, abrasive agents, drying agents, and fluids for energy production units.

The manufacture of HCFO-1233zdE is accompanied by a multitude of by-products having a boiling point close to HCFO-1233zdE. This results in purification steps which are relatively complex and costly. The difficulties encountered during the purification of HCFO-1233zdE generally entail an appreciable loss of target product. In addition, the by-products may form azeotropic compositions with the HCFO-1233zdE, making separation by simple distillation very difficult, or even impossible. The purification steps include in particular a step of neutralizing the crude product at the outlet of the reactor in order to remove the residual traces of acids, i.e. HCl and HF. This neutralization step is generally carried out by means of a basic solution.

Known in particular from WO 2015/167784 is a process for separating HCFO-1233zd and HF by a series of steps including, for example, a distillation in order to remove the HCl at the top of the distillation column, the cooling of the stream at the column bottom in order to obtain a two-phase mixture, the separation of the two phases and the treatment of one of said phases with an adsorbent which may be a liquid adsorbent (water, NaOH or KOH).

Also known from WO 2016/148957 is a process for purifying HCFO-1233zdE comprising a washing step, a condensation and phase separation step and, finally, a drying step. Also known from WO 2014/010530, WO 2014/189674 and WO 2014/099464 is a process for preparing HCFO-1233zd comprising a purification step such as washing with water or washing with a basic solution.

During the purification of HCFO-1233zd, the treatment carried out in order to remove acidic impurities such as HF or HCl may contribute to the formation of certain impurities. Thus, new acid impurity neutralization conditions must be implemented in order to minimize the degradation of HCFO-1233zdE. There is a need for an efficient process for purifying trans-1-chloro-3,3,3-trifluoropropene which minimizes the production of by-products or other impurities resulting from a dehydrochlorination reaction.

SUMMARY OF THE INVENTION

According to a first aspect, the present invention provides a process for neutralizing a composition A comprising 1-chloro-3,3,3-trifluoropropene, 1,1-dichloro-1,3,3-trifluoropropane and one or more acid compound(s) of formula HX with X=F or Cl; said process comprising the step a) of bringing said composition A into contact with a solution B under conditions capable of limiting the formation of 1-chloro-1,3,3-trifluoropropene.

Preferably, the solution B is a basic solution. The solution B aims to neutralize all or part of the acid compound(s) of formula HX as defined above.

The applicant has observed that the compound 1-chloro-1,3,3-trifluoropropene is formed in a not insignificant amount during the production and purification of 1-chloro-3,3,3-trifluoropropene, in particular during the step of neutralizing the acid compounds present in the reaction medium. The applicant has surprisingly identified operating conditions which make it possible to limit the formation of 1-chloro-1,3,3-trifluoropropene during the purification process, in particular during the neutralization step.

According to one preferred embodiment, said conditions comprise the implementation of step a) with a solution B comprising an alkali metal hydroxide, preferably with a solution B comprising NaOH or KOH; in particular with a solution B comprising NaOH.

According to one preferred embodiment, said solution B of step a) is an aqueous solution.

According to one preferred embodiment, the alkali metal hydroxide content is from 2 to 40% by weight based on the total weight of said solution B.

According to one preferred embodiment, step a) is carried out at a temperature from 10° C. to 90° C.

According to one preferred embodiment, step a) is carried out with a residence time of between 1 second and 5 minutes.

According to one preferred embodiment, the 1-chloro-3,3-trifluoropropene is in the trans form.

According to one preferred embodiment, step a) makes it possible to obtain a gas stream C comprising 1-chloro-3,3,3-trifluoropropene, 1-chloro-1,3,3-trifluoropropene and 1,1-dichloro-1,3,3-trifluoropropane.

According to one preferred embodiment, the 1-chloro-1,3,3-trifluoropropene is obtained by dehydrochlorination of 1,1-dichloro-1,3,3-trifluoropropane. The 1-chloro-1,3,3-trifluoropropene is obtained by dehydrochlorination of 1,1-dichloro-1,3,3-trifluoropropane in a basic medium.

According to a second aspect, the present invention provides a process for producing 1-chloro-3,3,3-trifluoropropene comprising the steps of:
i) bringing hydrofluoric acid (HF) into contact, in a reactor, with a starting composition comprising at least one chlorinated compound selected from the group consisting of 1,1,3,3-tetrachloropropene, 1,3,3,3-tetrachloropropene and a mixture of the two, under conditions sufficient to obtain a stream D comprising 1-chloro-3,3,3-trifluoropropene, 1,1-dichloro-1,3,3-trifluoropropane, HF and/or HCl;

ii) carrying out the neutralization process according to the present invention starting from the stream D obtained in step i).

According to a third aspect, the present invention provides a composition comprising 1-chloro-3,3,3-trifluoropropene and 1-chloro-1,3,3-trifluoropropene, the molar content of 1-chloro-1,3,3-trifluoropropene being less than 110 ppm in said composition.

According to one preferred embodiment, the molar content of 1-chloro-3,3,3-trifluoropropene in said composition is greater than 90%.

According to one preferred embodiment, the molar content of 1-chloro-1,3,3-trifluoropropene is less than 100 ppm, preferably less than 90 ppm, more preferentially less than 80 ppm, in particular less than 70 ppm, more particularly less than 60 ppm, preferably less than 50 ppm.

According to one preferred embodiment, the composition also comprises 1,1-dichloro-1,3,3-trifluoropropane.

According to another aspect, the present invention provides a process for preparing 1-chloro-1,3,3-trifluoropropene by dehydrochlorination of 1,1-dichloro-1,3,3-trifluoropropane in the presence of a basic solution.

According to one preferred embodiment, the basic solution comprises an alkali or alkaline earth metal hydroxide; preferably, the basic solution comprises NaOH or KOH.

According to one preferred embodiment, the process is carried out at a temperature of between 10° C. and 150° C., preferably between 10 90° C.

DETAILED DESCRIPTION OF THE PRESENT INVENTION

According to a first aspect, the present invention relates to a process for neutralizing a composition A. Preferably, the present invention relates to a process for neutralizing said composition under conditions capable of limiting the formation of 1-chloro-1,3,3-trifluoropropene during the neutralization of the acid compounds resulting from the production of 1-chloro-3,3,3-trifluoropropene. Preferably, said composition A comprises 1-chloro-3,3,3-trifluoropropene, 1,1-dichloro-1,3,3-trifluoropropane and an acid compound of formula HX with X=F or Cl. Preferably, said process comprises step a) of bringing said composition A into contact with a solution B under conditions capable of limiting the formation of 1-chloro-1,3,3-trifluoropropene. Preferably, the solution B is a basic solution.

Preferably, said conditions comprise step a) of bringing said composition A into contact with a solution B comprising an alkali metal hydroxide under conditions capable of limiting the formation of 1-chloro-1,3,3-trifluoropropene.

Thus, the present invention provides a process for neutralizing a composition A comprising 1-chloro-3,3,3-trifluoropropene, 1,1-dichloro-1,3,3-trifluoropropane and an acid compound of formula HX with X=F or Cl; said process comprising step a) of bringing said composition A into contact with a solution B comprising an alkali metal hydroxide under conditions capable of limiting the formation of 1-chloro-1,3,3-trifluoropropene.

Preferably, said conditions comprise the implementation of step a) with a solution B comprising NaOH or KOH as alkali metal hydroxide.

Thus, the present invention provides a process for neutralizing a composition A comprising 1-chloro-3,3,3-trifluoropropene, 1,1-dichloro-1,3,3-trifluoropropane and an acid compound of formula HX with X=F or Cl; said process comprising step a) of bringing said composition A into contact with a solution B comprising and NaOH or KOH.

Preferably, said conditions comprise the implementation of step a) with a solution B comprising NaOH as alkali metal hydroxide.

Thus, the present invention provides a process for neutralizing a composition A comprising 1-chloro-3,3,3-trifluoropropene, 1,1-dichloro-1,3,3-trifluoropropane and an acid compound of formula HX with X=F or Cl; said process comprising step a) of bringing said composition A into contact with a solution B comprising NaOH.

According to one preferred embodiment, the alkali metal hydroxide content is between 2 and 40% by weight based on the total weight of said solution. B. In particular, the alkali metal hydroxide content is from 5 to 25% by weight based on the total weight of said solution B. More particularly, the alkali metal hydroxide content is from 10 to 25% by weight based on the total weight of said solution B. The alkali metal hydroxide content may be from 15 to 25% by weight based on the total weight of said solution B.

Thus, in one preferred embodiment, said solution B comprises NaOH in a weight content of from 2 to 40% by weight based on the total weight of said solution B, advantageously from 5 to 25% by weight based on the total weight of said solution B, in particular from 10 to 25% by weight based on the total weight of said solution B. The NaOH content can be from 15 to 25% by weight based on the total weight of said solution B.

Preferably, said solution B of step b) is an aqueous solution, in particular a basic aqueous solution.

Advantageously, said solution B is an aqueous solution, preferably a basic aqueous solution, comprising an alkali metal hydroxide consisting of NaOH. Preferably, said solution B is an aqueous solution, preferably a basic aqueous solution, comprising at least one alkali metal hydroxide consisting of NaOH; the weight content of NaOH in said solution being from 2 to 40% by weight, in particular the weight content of NaOH in said solution is from 5 to 25% by weight, more particularly from 10 to 25% or from 15 to 25% by weight based on the total weight of said solution B.

Said composition A may optionally comprise 1-chloro-1,3,3-trifluoropropene. According to one preferred embodiment, step a) makes it possible to obtain a gas stream C comprising 1-chloro-3,3,3-trifluoropropene, 1-chloro-1,3,3-trifluoropropene and 1,1-dichloro-1,3,3-trifluoropropane.

Preferably, the molar content of 1-chloro-1,3,3-trifluoropropene in said stream C is less than or equal to 110 ppm, advantageously less than or equal to 100 ppm, preferably less than or equal to 90 ppm, more preferentially less than or equal to 80 ppm, in particular less than or equal to 70 ppm, more particularly less than or equal to 60 ppm, preferably less than or equal to 50 ppm.

Preferably, the molar content of 1-chloro-3,3,3-trifluoropropene in said stream C is greater than 85%, advantageously greater than 87%, preferably greater than 90%, more preferentially greater than 92%, in particular greater than 95%, more particularly greater than 97%, preferably greater than 99%.

Thus, said stream C may comprise a molar content of 1-chloro-3,3,3-trifluoropropene of greater than 85% and a molar content of 1-chloro-1,3,3-trifluoropropene of less than or equal to 110 ppm, advantageously less than or equal to 100 ppm, preferably less than or equal to 90 ppm, more preferentially less than 80 ppm, in particular less than 70 ppm, more particularly less than or equal to 60 ppm, preferably less than or equal to 50 ppm.

Advantageously, said stream C may comprise a molar content of 1-chloro-3,3,3-trifluoropropene of greater than 87% and a molar content of 1-chloro-1,3,3-trifluoropropene of less than or equal to 110 ppm, advantageously less than or equal to 100 ppm, preferably less than or equal to 90 ppm, more preferentially less than or equal to 80 ppm, in particular less than or equal to 70 ppm, more particularly less than or equal to 60 ppm, preferably less than or equal to 50 ppm.

Preferably, said stream C may comprise a molar content of 1-chloro-3,3,3-trifluoropropene of greater than 90% and a molar content of 1-chloro-1,3,3-trifluoropropene of less than or equal to 110 ppm, advantageously less than or equal to 100 ppm, preferably less than or equal to 90 ppm, more preferably less than or equal to 80 ppm, in particular less than or equal to 70 ppm, more particularly less than or equal to 60 ppm, preferably less than or equal to 50 ppm.

More preferentially, said stream C may comprise a molar content of 1-chloro-3,3,3-trifluoropropene of greater than 92% and a molar content of 1-chloro-1,3,3-trifluoropropene of less than or equal to 110 ppm, advantageously less than or equal to 100 ppm, preferably less than or equal to 90 ppm, more preferentially less than or equal to 80 ppm, in particular less than or equal to 70 ppm, more particularly less than or equal to 60 ppm, preferably less than or equal to 50 ppm.

In particular, said stream C may comprise a molar content of 1-chloro-3,3,3-trifluoropropene of greater than 95% and a molar content of 1-chloro-1,3,3-trifluoropropene of less than or equal to 110 ppm, advantageously less than or equal to 100 ppm, preferably less than or equal to 90 ppm, more preferentially less than or equal to 80 ppm, in particular less than or equal to 70 ppm, more particularly less than or equal to 60 ppm, preferably less than or equal to 50 ppm.

More particularly, said stream C may comprise a molar content of 1-chloro-3,3,3-trifluoropropene of greater than 97% and a molar content of 1-chloro-1,3,3-trifluoropropene of less than or equal to 110 ppm, advantageously less than or equal to 100 ppm, preferably less than or equal to 90 ppm, more preferentially less than or equal to 80 ppm, in particular less than or equal to 70 ppm, more particularly less than or equal to 60 ppm, preferably less than or equal to 50 ppm.

Preferably, said stream C may comprise a molar content of 1-chloro-3,3,3-trifluoropropene of greater than 99% and a molar content of 1-chloro-1,3,3-trifluoropropene of less than or equal to 110 ppm, advantageously less than or equal to 100 ppm, preferably less than or equal to 90 ppm, more preferably less than or equal to 80 ppm, in particular less than or equal to 70 ppm, more particularly less than or equal to 60 ppm, preferably less than or equal to 50 ppm.

The molar content of 1,1-dichloro-1,3,3-trifluoropropane in said stream C can be between 10 and 200 ppm, preferably between 20 and 150 ppm, in particular between 50 and 100 ppm.

Thus, said stream C may comprise a molar content of 1-chloro-3,3,3-trifluoropropene of greater than 85% and a molar content of 1-chloro-1,3,3-trifluoropropene of less than or equal to 110 ppm, advantageously less than or equal to 100 ppm, preferably less than or equal to 90 ppm, more preferentially less than 80 ppm, in particular less than 70 ppm, more particularly less than or equal to 60 ppm, preferably less than or equal to 50 ppm; and a molar content of 1,1-dichloro-1,3,3-trifluoropropane of between 10 and 200 ppm, preferably between 20 and 150 ppm, in particular between 50 and 100 ppm.

Advantageously, said stream C may comprise a molar content of 1-chloro-3,3,3-trifluoropropene of greater than 87% and a molar content of 1-chloro-1,3,3-trifluoropropene of less than or equal to 110 ppm, advantageously less than or equal to 100 ppm, preferably less than or equal to 90 ppm, more preferentially less than or equal to 80 ppm, in particular less than or equal to 70 ppm, more particularly less than or equal to 60 ppm, preferably less than or equal to 50 ppm; and a molar content of 1,1-dichloro-1,3,3-trifluoropropane of between 10 and 200 ppm, preferably between 20 and 150 ppm, in particular between 50 and 100 ppm.

Preferably, said stream C may comprise a molar content of 1-chloro-3,3,3-trifluoropropene of greater than 90% and a molar content of 1-chloro-1,3,3-trifluoropropene of less than or equal to 110 ppm, advantageously less than or equal to 100 ppm, preferably less than or equal to 90 ppm, more preferentially less than or equal to 80 ppm, in particular less than or equal to 70 ppm, more particularly less than or equal to 60 ppm, preferably less than or equal to 50 ppm; and a molar content of 1,1-dichloro-1,3,3-trifluoropropane of between 10 and 200 ppm, preferably between 20 and 150 ppm, in particular between 50 and 100 ppm.

More preferentially, said stream C may comprise a molar content of 1-chloro-3,3,3-trifluoropropene of greater than 92% and a molar content of 1-chloro-1,3,3-trifluoropropene of less than or equal to 110 ppm, advantageously less than or equal to 100 ppm, preferably less than or equal to 90 ppm, more preferentially less than or equal to 80 ppm, in particular less than or equal to 70 ppm, more particularly less than or equal to 60 ppm, preferably less than or equal to 50 ppm; and a molar content of 1,1-dichloro-1,3,3-trifluoropropane of between 10 and 200 ppm, preferably between 20 and 150 ppm, in particular between 50 and 100 ppm.

In particular, said stream C may comprise a molar content of 1-chloro-3,3,3-trifluoropropene of greater than 95% and a molar content of 1-chloro-1,3,3-trifluoropropene of less than or equal to 110 ppm, advantageously less than or equal to 100 ppm, preferably less than or equal to 90 ppm, more preferentially less than or equal to 80 ppm, in particular less than or equal to 70 ppm, more particularly less than or equal to 60 ppm, preferably less than or equal to 50 ppm; and a molar content of 1,1-dichloro-1,3,3-trifluoropropane of between 10 and 200 ppm, preferably between 20 and 150 ppm, in particular between 50 and 100 ppm.

More particularly, said stream C may comprise a molar content of 1-chloro-3,3,3-trifluoropropene of greater than 97% and a molar content of 1-chloro-1,3,3-trifluoropropene of less than or equal to 110 ppm, advantageously less than or equal to 100 ppm, preferably less than or equal to 90 ppm, more preferentially less than or equal to 80 ppm, in particular less than or equal to 70 ppm, more particularly less than or equal to 60 ppm, preferably less than or equal to 50 ppm; and a molar content of 1,1-dichloro-1,3,3-trifluoropropane of between 10 and 200 ppm, preferably between 20 and 150 ppm, in particular between 50 and 100 ppm.

Preferably, said stream C may comprise a molar content of 1-chloro-3,3,3-trifluoropropene of greater than 99% and a molar content of 1-chloro-1,3,3-trifluoropropene of less than or equal to 110 ppm, advantageously less than or equal to 100 ppm, preferably less than or equal to 90 ppm, more preferentially less than or equal to 80 ppm, in particular less than or equal to 70 ppm, more particularly less than or equal to 60 ppm, preferably less than or equal to 50 ppm; and a molar content of 1,1-dichloro-1,3,3-trifluoropropane of between 10 and 200 ppm, preferably between 20 and 150 ppm, in particular between 50 and 100 ppm.

In particular, in any one of said streams C defined above or in any one of the compositions A as defined above, 1-chloro-3,3,3-trifluoropropene represents at least 90 mol % of trans-1-chloro-3,3,3-trifluoropropene, more particularly at least 92 mol % of trans-1-chloro-3,3,3-trifluoropropene, preferably at least 95 mol % of trans-1-chloro-3,3,3-trifluoropropene; the remainder being represented by the cis-1-chloro-3,3,3-trifluoropropene isomer. Preferably, in any one of said streams C defined above or in any one of the compositions A as defined above, 1-chloro-3,3,3-trifluoropropene is trans-1-chloro-3,3,3-trifluoropropene.

Said solution B may optionally comprise reducing agents, such as sulfite or bisulfite salts. Alternatively, said solution B can be an organic solution containing a solvent. The solvent is defined as an inert organic compound wherein 1-chloro-3,3,3-trifluoropropene is at least partially soluble. The solvent is preferably selected from the group consisting of hydrocarbons, ethers, alcohols, alkyl halides, substituted or unsubstituted benzenes, alkyl nitrile, amides, sulfoxides, sulfones, phosphate esters and mixtures thereof. Preferably, the solvent is selected from ethers, alcohols, alkyl halides, substituted or unsubstituted benzenes, alkyl nitrile, amides, sulfoxides, sulfones, and mixtures thereof. The ethers include acyclic alkyl ethers, cyclic ethers, perfluorinated ethers, glyme, diglyme, triglyme, tetraglyme, and mixtures thereof. Acyclic alkyl ethers include dimethyl ether, ethyl ether, methyl ethyl ether, and mixtures thereof. The cyclic ethers include 2-methyltetrahydrofuran, tetrahydrofuran, tetrahydropyran, 1,4-dioxane, and mixtures thereof. The perfluorinated ethers include perfluoro-N-methyl morpholine, perfluorotetrahydrofuran, and mixtures thereof. The alcohols include alkyl alcohols, glycols, glycerol, and mixtures thereof. The alcohol alkyls include methanol, ethanol, propanol, isopropanol, 2-methyl-2-propanol, cyclohexanol, and mixtures thereof. Examples of glycol include ethylene glycol, propylene glycol, diethylene glycol, and mixtures thereof. The substituted and unsubstituted benzenes include alkylbenzenes, halobenzenes, benzonitrile phenol, anisole, biphenyl, nitrobenzene, and mixtures thereof. The alkylbenzenes include toluene, ethylbenzene, o-xylene, m-xylene, p-xylene, mesitylene, durene, 2-phenylhexane, and mixtures thereof. The halobenzenes include fluorobenzene, chlorobenzene, 1,2-dichlorobenzene, 1,4-dichlorobenzene, and mixtures thereof. The alkyl halides include dichloromethane, chloroform, carbon tetrachloride, chloroethane, 1,2-dichloroethane, and mixtures thereof. The alkyl nitriles include acetonitrile, butyronitrile, methylglutaronitrile, adiponitrile, and mixtures thereof. The amides include N,N-dimethyl formamide, N,N-dimethyl-acetamide, N-methyl-2-pyrrolidone, and mixtures thereof. The sulfoxides include dimethyl sulfoxide. The sulfones include sulfolane.

When said solution B is an organic solution, this comprises at least one alkali metal hydroxide consisting of NaOH, preferably in a weight content of 2 to 40% based on the total weight of said solution B, in particular a weight content of 5 to 20% by weight based on the total weight of said solution B.

Preferably, whatever the solution B, step a) of the present process is carried out at a temperature of from 10° C. to 90° C., advantageously from 10° C. to 80° C., preferably from 10° C. to 70° C., in particular from 10° C. to 60° C.

Preferably, step a) is carried out with a residence time of between 1 second and 5 minutes, in particular between 5 seconds and 5 minutes, more particularly between 10 seconds and 5 minutes, preferably between 15 seconds and 5 minutes.

According to a second aspect of the present invention, a process for producing 1-chloro-3,3,3-trifluoropropene is provided.

Said process for producing 1-chloro-3,3,3-trifluoropropene comprises the steps of:

i) bringing hydrofluoric acid (HF) into contact, in a reactor, with a starting composition comprising at least one chlorinated compound selected from the group consisting of 1,1,3,3-tetrachloropropene, 1,3,3,3-tetrachloropropene and a mixture of the two, under conditions sufficient to obtain a stream D comprising 1-chloro-3,3,3-trifluoropropene, 1,1-dichloro-1,3,3-trifluoropropane, HF and/or HCl;

ii) carrying out the neutralization process according to the present invention starting from the stream D obtained in step i).

In particular, in this production process as described above and below, 1-chloro-3,3,3-trifluoropropene represents at least 90 mol % of trans-1-chloro-3,3,3-trifluoropropene, more particularly at least 92 mol % of trans-1-chloro-3,3,3-trifluoropropene, preferably at least 95 mol % of trans-1-chloro-3,3,3-trifluoropropene; the remainder being represented by the cis-1-chloro-3,3,3-trifluoropropene isomer. Preferably, in this production process as described above and below, 1-chloro-3,3,3-trifluoropropene is trans-1-chloro-3,3,3-trifluoropropene.

Preferably, said step i) is carried out in a liquid phase, preferably low in HF.

According to one preferred embodiment, said starting composition comprises at least 10% by weight of said at least one of the chlorinated compounds, based on the total weight of said starting composition. Said starting composition advantageously comprises at least 15% by weight of said at least one chlorinated compound, preferably at least 20% by weight of said at least one chlorinated compound, more preferably at least 25% by weight of said at least one chlorinated compounds, in particular at least 30% by weight of said at least one chlorinated compound, more particularly at least 35% by weight of said at least one chlorinated compound, preferentially at least 40% by weight of said at least one chlorinated compound, advantageously preferably at least 45% by weight of said at least one chlorinated compound, preferably preferentially at least 50% by weight of said at least one chlorinated compound, particularly preferably at least 55% by weight of said at least one chlorinated compound, based on the total weight of said starting composition.

Said starting composition preferably comprises at least 60% by weight or at least 65% by weight or at least 70% by weight or at least 75% by weight or at least 80% by weight or at least 85% by weight or at least 90% by weight or at least 95% by weight or at least 99% by weight of said at least one chlorinated compound, based on the total weight of said starting composition.

According to one preferred embodiment, said at least one chlorinated compound is 1,1,3,3-tetrachloropropene (1230za). Said process therefore comprises a step i) of contacting hydrofluoric acid (HF) in a reactor with a starting composition comprising 1,1,3,3-tetrachloropropene (1230za) to produce a stream D comprising 1-chloro-3,3,3-trifluoropropene (1233zd), HF and HCl; said step i) is carried out in a low-HF liquid phase as defined below. The present process preferably enables the production of 1-chloro-3,3,3-trifluoropropene in the form of a mixture of the two cis and trans isomers. The present process enables majority production of the trans-1-chloro-3,3,3-trifluoropropene isomer, preferably at least 90 mol % of the trans isomer.

Said starting composition therefore comprises at least 10% by weight of 1,1,3,3-tetrachloropropene, based on the total weight of said starting composition. Said starting composition advantageously comprises at least 15% by weight of 1,1,3,3-tetrachloropropene, preferably at least 20% by weight of 1,1,3,3-tetrachloropropene, more preferably at least 25% by weight of 1,1,3,3-tetrachloropropene, in particular at least 30% by weight of 1,1,3,3-tetrachloropropene, more particularly at least 35% by weight of 1,1,3,3-tetrachloropropene, preferentially at least 40% by weight of 1,1,3,3-tetrachloropropene, advantageously preferentially at least 45% by weight of 1,1,3,3-tetrachloropropene, preferably preferentially at least 50% by weight of 1,1,3,3-tetrachloropropene, particularly preferentially at least 55% by weight of 1,1,3,3-tetrachloropropene, based on the total weight of said starting composition.

Said starting composition preferably comprises at least 60% by weight or at least 65% by weight or at least 70% by weight or at least 75% by weight or at least 80% by weight or at least 85% by weight or at least 90% by weight or at least 95% by weight or at least 99% by weight of 1,1,3,3-tetrachloropropene, based on the total weight of said starting composition.

According to one preferred embodiment, said starting composition comprises less than 15% by weight of HF, based on the total weight of said starting composition, advantageously less than 10% by weight of HF, preferably less than 8% by weight of HF, more preferably less than 6% by weight of HF, in particular less than 5% by weight of HF, more particularly less than 4% by weight of HF, preferentially less than 2% by weight of HF, based on the total weight of said starting composition. In the present process, preferably, the starting composition is devoid of HF. The term "devoid" signifies an amount by weight of less than 500 ppm, preferably less than 100 ppm, more particularly less than 10 ppm.

Said low-HF liquid phase is preferably a liquid phase comprising less than 15% by weight of HF, advantageously less than 10% by weight of HF, preferably less than 8% by weight of HF, more preferably less than 6% by weight of HF, in particular less than 5% by weight of HF, more particularly less than 4% by weight of HF, preferentially less than 2% by weight of HF, based on the total weight of said liquid phase.

While step i) is being carried out, said liquid phase may comprise at least 10% by weight of compounds of formula (I) $C_3H_nF_mCl_p$ (I) wherein n is an integer from 0 to 8, m is an integer from 0 to 8, and p is an integer from 0 to 8; preferably, n is an integer from 0 to 8, m is an integer from 0 to 6, and p is an integer from 0 to 6. Compounds of formula (I) may, for example, be $C_3Cl_6$, $C_3H_4Cl_4$ or $C_3H_3Cl_5$. Preferably, while step i) is being carried out, said liquid phase may comprise at least 10% by weight of compounds of formula (I) $C_3H_nF_mCl_p$ (I) wherein n is an integer from 1 to 8, m is an integer from 0 to 4, and p is an integer from 0 to 4; preferably, n is an integer from 1 to 4, m is an integer from 0 to 3, and p is an integer from 2 to 4. The compounds of formula (I) may be propane- or propene-type compounds comprising one or more chlorine atoms and/or one or more fluorine atoms. Said liquid phase may preferably comprise at least 10% by weight of compounds of formula (I) selected from the group consisting of $C_3H_2Cl_4$, $C_3H_2Cl_3F$, $C_3H_2Cl_2F_2$, $C_3H_3Cl_5$, $C_3H_3Cl_4F$, $C_3H_3Cl_3F_2$, and $C_3H_3Cl_2F_3$. In particular, said liquid phase may comprise at least 10% by weight of compounds of formula (I) selected from the group consisting of $C_3H_2Cl_4$, $C_3H_2Cl_3F$, and $C_3H_2Cl_2F_2$. Said liquid phase may comprise at least 15% by weight of compounds of formula (I) $C_3H_nF_mCl_p$ (I) wherein n is an integer from 0 to 8, m is an integer from 0 to 8, and p is an integer from 0 to 8; preferably, n is an integer from 0 to 8, m is an integer from 0 to 6, and p is an integer from 0 to 6. More particularly, while step i) is being carried out, said liquid phase may comprise at least 15% by weight of compounds of formula (I) $C_3H_nF_mCl_p$ (I) wherein n is an integer from 1 to 8, m is an integer from 0 to 4, and p is an integer from 0 to 4; preferably, n is an integer from 1 to 4, m is an integer from 0 to 3, and p is an integer from 2 to 4. Said liquid phase may preferably comprise at least 15% by weight of compounds of formula (I) selected from the group consisting of $C_3H_2Cl_4$, $C_3H_2Cl_3F$, $C_3H_2Cl_2F_2$, $C_3H_3Cl_5$, $C_3H_3Cl_4F$, $C_3H_3Cl_3F_2$, and $C_3H_3Cl_2F_3$. In particular, said liquid phase may comprise at least 15% by weight of compounds of formula (I) selected from the group consisting of $C_3H_2Cl_4$, $C_3H_2Cl_3F$, and $C_3H_2Cl_2F_2$. Said liquid phase may comprise at least 20%, at least 30%, at least 40%, at least 50%, at least 60%, at least 70%, at least 80% or at least 90% by weight of compounds of formula (I) $C_3H_nF_mCl_p$ (I) wherein n is an integer from 0 to 8, m is an integer from 0 to 8, and p is an integer from 0 to 8; preferably, n is an integer from 0 to 8, m is an integer from 0 to 6, and p is an integer from 0 to 6. Said liquid phase may comprise at least 20%, at least 30%, at least 40%, at least 50%, at least 60%, at least 70%, at least 80% or at least 90% by weight of compounds of formula (I) $C_3H_nF_mCl_p$ (I) wherein n is an integer from 1 to 8, m is an integer from 0 to 4, and p is an integer from 0 to 4; preferably, n is an integer from 1 to 4, m is an integer from 0 to 3, and p is an integer from 2 to 4. Said liquid phase may preferably comprise at least 20%, at least 30%, at least 40%, at least 50%, at least 60%, at least 70%, at least 80% or at least 90% by weight of compounds of formula (I) selected from the group consisting of $C_3H_2Cl_4$, $C_3H_2Cl_3F$, $C_3H_2Cl_2F_2$, $C_3H_3Cl_5$, $C_3H_3Cl_4F$, $C_3H_3Cl_3F_2$, and $C_3H_3Cl_2F_3$. In particular, said liquid phase may comprise at least 20%, at least 30%, at least 40%, at least 50%, at least 60%, at least 70%, at least 80% or at least 90% by weight of compounds of formula (I) selected from the group consisting of $C_3H_2Cl_4$, $C_3H_2Cl_3F$, and $C_3H_2Cl_2F_2$.

Step i) is preferably carried out in the absence of catalyst.

Step i) may alternatively be carried out in the presence of a catalyst. The catalyst may be a $TiCl_4$ or $SbCl_5$ catalyst. The catalyst may also be an ionic liquid. The ionic liquids which may be suitable are Lewis acid derivatives based on aluminum, titanium, niobium, tantalum, tin, antimony, nickel, zinc or iron. The term "ionic liquids" refers to nonaqueous salts of ionic nature which are liquid at moderate temperatures (preferably below 120° C.). Ionic liquids preferably result from the reaction between an organic salt and an inorganic compound. Ionic liquids are preferably obtained by reaction of at least one halogen or oxyhalogen Lewis acid based on aluminum, titanium, niobium, tantalum, tin, antimony, nickel, zinc or iron with a salt of general formula $Y^+A^-$, wherein $A^-$ denotes a halide anion (bromide, iodide and, preferably, chloride or fluoride) or hexafluoroantimonate ($SbF_6^-$) and $Y^+$ a quaternary ammonium, quaternary phosphonium or ternary sulfonium cation. The halogen Lewis acid based on aluminum, titanium, niobium, tantalum, antimony, nickel, zinc or iron may be a chloro, bromo, fluoro or mixed derivative, for example a chlorofluoro acid. Mention may be made more particularly of the chlorides, fluorides or chlorofluorides having the following formulae:

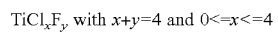
$TiCl_xF_y$ with $x+y=4$ and $0<=x<=4$

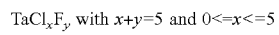
$TaCl_xF_y$ with $x+y=5$ and $0<=x<=5$

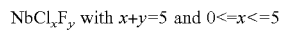
$NbCl_xF_y$ with $x+y=5$ and $0<=x<=5$

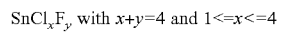
$SnCl_xF_y$ with $x+y=4$ and $1<=x<=4$

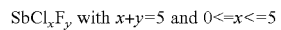
$SbCl_xF_y$ with $x+y=5$ and $0<=x<=5$

AlCl$_x$F$_y$ with x+y=3 and 0<=x<=3

NiCl$_x$F$_y$ with x+y=2 and 0<=x<=2

FeCl$_x$F$_y$ with x+y=3 and 0<=x<=3

As examples of such compounds, mention may be made of the following compounds: TiCl$_4$, TiF$_4$, TaCl$_5$, TaF$_5$, NbCl$_5$, NbF$_5$, SbCl$_5$, SbCl$_4$F, SbCl$_3$F$_2$, SbCl$_2$F$_3$, SbClF$_4$, SbF$_5$, and mixtures thereof. The following compounds are preferentially used: TiCl$_4$, TaCl$_5$+TaF$_5$, NbCl$_5$+NbF$_5$, SbCl$_5$, SbFCl$_4$, SbF$_2$Cl$_3$, SbF$_3$Cl$_2$, SbF$_4$Cl, SbF$_5$, and SbCl$_5$+SbF$_5$. The antimony-based compounds are more particularly preferred. As examples of oxyhalogen Lewis acids that may be used according to the invention, mention may be made of TiOCl$_2$, TiOF$_2$ and SbOCl$_x$F$_y$ (x+y=3). In the salt Y$^+$A$^-$, the cation Y$^+$ may correspond to one of the following general formulae: R$^1$R$^2$R$^3$R$^4$N$^+$, R$^1$R$^2$R$^3$R$^4$P$^+$, R$^1$R$^2$R$^3$S$^+$ wherein the symbols R$^1$ to R$^4$, which may be identical or different, each denote a saturated or unsaturated, cyclic or noncyclic, or aromatic hydrocarbyl, chlorohydrocarbyl, fluorohydrocarbyl, chlorofluorohydrocarbyl or fluorocarbyl group having from 1 to 10 carbon atoms, with one or more of these groups possibly also containing one or more heteroatoms such as N, P, S or O. The ammonium, phosphonium or sulfonium cation Y$^+$ may also form part of a saturated or unsaturated, or aromatic, heterocycle having from 1 to 3 nitrogen, phosphorus or sulfur atoms, and may correspond to one or other of the following general formulae:

[Chem 1]

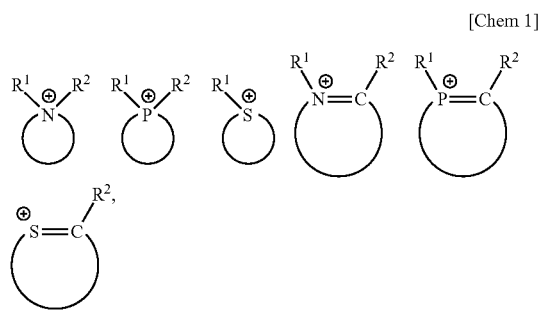

wherein R$^1$ and R$^2$ are as defined previously. A salt containing two or three ammonium, phosphonium or sulfonium sites in its formula may also be suitable for use. As examples of salts Y$^+$A$^-$, mention may be made of tetraalkylammonium chlorides and fluorides, tetraalkylphosphonium chlorides and fluorides, and trialkylsulfonium chlorides and fluorides, alkylpyridinium chlorides and fluorides, dialkylimidazolium chlorides, fluorides and bromides, and trialkylimidazolium chlorides and fluorides. Trimethylsulfonium fluoride or chloride, N-ethylpyridinium chloride or fluoride, N-butylpyridinium chloride or fluoride, 1-ethyl-3-methylimidazolium chloride or fluoride, and 1-butyl-3-methylimidazolium chloride or fluoride are more particularly valued. The ionic liquids may be prepared in a manner known per se by appropriate mixing of the halogen or oxyhalogen Lewis acid and the organic salt Y$^+$A$^-$. Reference may be made notably to the method described in document WO 01/81353. The catalyst may alternatively be triflic or trifluoroacetic acid as stated in U.S. Pat. No. 6,166,274.

According to one preferred embodiment, as well as the 1-chloro-3,3,3-trifluoropropene, the stream D comprises coproducts selected from the group consisting of 1,3,3,3-tetrafluoropropene and 1,1,1,3,3-pentafluoropropane.

According to one preferred embodiment, the amount, in the stream D, of coproducts selected from the group consisting of 1,3,3,3-tetrafluoropropene and 1,1,1,3,3-pentafluoropropane is less than 0.5 mol %. The 1,3,3,3-tetrafluoropropene content of said stream D is preferably less than 0.5 mol %, more preferably less than 0.4 mol %, more particularly less than 0.3 mol %. The 1,1,1,3,3-pentafluoropropane content of said stream D is preferably less than 0.1 mol %, more preferably less than 0.075 mol %, more particularly less than 0.05 mol %.

Step i) is preferably carried out at a temperature of 50° C. to 150° C., preferably at a temperature of 75° C. to 100° C.

Step i) is preferably carried out at a pressure of 5 to 20 bara, preferably at a pressure of 10 to 18 bara, more particularly of 12 to 18 bara.

The molar HF/[chlorinated compounds] ratio at the entry of the reactor is preferably between 5 and 10, more preferably between 5 and 7, more particularly between 5 and 6. More particularly, when said chlorinated compound in the starting composition is 1,1,3,3-tetrachloropropene (1230za), the molar HF/1230za ratio is between 5 and 10, more preferably between 5 and 7, more particularly between 5 and 6.

The hydrofluoric acid and said starting composition can be introduced into the reactor via a static mixer. Preferably, the hydrofluoric acid is heated before it is introduced into the reactor and thus before the implementation of step i). Preferably, the hydrofluoric acid is heated to a temperature of from 100° C. to 170° C., preferably from 120° C. to 170° C., in particular from 125° C. to 165° C., more particularly from 125° C. to 155° C.

According to one particular embodiment, the stream D obtained in step i) can be subjected to purification steps prior to the implementation of step ii). Alternatively, the stream D obtained in step i) can be used directly in step ii).

Thus, said production process can comprise a step i'), subsequent to step i) and prior to step ii), comprising a step of treating the stream D to give a stream D1 comprising 1-chloro-3,3,3-trifluoropropene, HCl and HF and a stream D2 comprising at least 50% by weight of HF, for example preferably at least 70% by weight of HF. The treatment step (i') is preferably a reflux column, carried out advantageously at a temperature of between 30 and 120° C. to give the stream D2, which is recycled to the reactor.

According to one particular embodiment, said process for producing 1-chloro-3,3,3-trifluoropropene according to the present invention comprises the steps of:
  i) bringing the hydrofluoric acid (HF) into contact, in a reactor, with a starting composition comprising at least one chlorinated compound selected from the group consisting of 1,1,3,3-tetrachloropropene, 1,3,3,3-tetrachloropropene and a mixture of the two, to obtain a stream D comprising 1-chloro-3,3,3-trifluoropropene, HF and HCl;
  i') a step of treating the stream D to give a stream D1 comprising 1-chloro-3,3,3-trifluoropropene, HCl and HF and a stream D2 comprising at least 50% by weight of HF;
  ii) carrying out the neutralization process according to the present invention starting from the stream D1 obtained in step i').

The present production process can also comprise a step ii') subsequent to step i') and prior to step ii). Preferably, said step ii') is a step of recovering hydrochloric acid from the stream D1 to form a stream D3 of HCl and a stream D4 comprising 1-chloro-3,3,3-trifluoropropene, HCl and HF. The recovery of HCl in step (ii') is preferably obtained by means of a distillation column equipped with a bottom reboiler and a top reflux system. The temperature at the bottom is advantageously between 20° C. and 110° C. The temperature at the top is advantageously between −50 and 0° C. The distillation of HCl is typically performed at a pressure of between 7 and 25 bar. This recovery step makes it possible to obtain a stream D4 wherein the amount of HCl is greatly reduced compared to the amount of HCl in the stream D1.

Thus, according to one particular embodiment, said process for producing 1-chloro-3,3,3-trifluoropropene according to the present invention comprises the steps of:
  i) bringing the hydrofluoric acid (HF) into contact, in a reactor, with a starting composition comprising at least one chlorinated compound selected from the group consisting of 1,1,3,3-tetrachloropropene, 1,3,3,3-tetrachloropropene and a mixture of the two, to obtain a stream D comprising 1-chloro-3,3,3-trifluoropropene, HF and HCl;
  i') treating the stream D to give a stream D1 comprising 1-chloro-3,3,3-trifluoropropene, HCl and HF and a stream D2 comprising at least 50% by weight of HF;
  ii') recovering hydrochloric acid from the stream D1 to form a stream D3 of HCl and a stream D4 comprising 1-chloro-3,3,3-trifluoropropene, HCl and HF;
  ii) carrying out the neutralization process according to the present invention starting from the stream D4 obtained in step ii') to form the gas stream C.

The present production process can also comprise a step iii') subsequent to step ii') and prior to step ii). Preferably, step iii') is a step of separating the stream D4 to form a stream D5 comprising at least 90% by weight, preferably at least 98% by weight and in particular at least 99% by weight of HF, and a stream D6 comprising 1-chloro-3,3,3-trifluoropropene, HCl and HF. The separation step is preferably a decantation, carried out at a temperature advantageously of between −50° C. and 50° C., preferably between −20° C. and 10° C.

Thus, according to one particular embodiment, said process for producing 1-chloro-3,3,3-trifluoropropene according to the present invention comprises the steps of:
  i) bringing the hydrofluoric acid (HF) into contact, in a reactor, with a starting composition comprising at least one chlorinated compound selected from the group consisting of 1,1,3,3-tetrachloropropene, 1,3,3,3-tetrachloropropene and a mixture of the two, to obtain a stream D comprising 1-chloro-3,3,3-trifluoropropene, HF and HCl;
  i') treating the stream D to give a stream D1 comprising 1-chloro-3,3,3-trifluoropropene, HCl and HF and a stream D2 comprising at least 50% by weight of HF;
  ii') recovering hydrochloric acid from the stream D1 to form a stream D3 of HCl and a stream D4 comprising 1-chloro-3,3,3-trifluoropropene, HCl and HF;
  iii') separating the stream D4 obtained in step ii') to form a stream D5 comprising at least 90% by weight and a stream D6 comprising 1-chloro-3,3,3-trifluoropropene, HCl and HF; ii) carrying out the neutralization process according to the present invention starting from the stream D6 obtained in step iii') to form the gas stream C.

The present production process can also comprise a step iv') subsequent to step iii') and prior to step ii). Preferably, step iv') is a step of washing with water. This step eliminates part of the HCl and of the HF contained in the stream D6.

Thus, according to one particular embodiment, said process for producing 1-chloro-3,3,3-trifluoropropene according to the present invention comprises the steps of:
  i) bringing the hydrofluoric acid (HF) into contact, in a reactor, with a starting composition comprising at least one chlorinated compound selected from the group consisting of 1,1,3,3-tetrachloropropene, 1,3,3,3-tetrachloropropene and a mixture of the two, to obtain a stream D comprising 1-chloro-3,3,3-trifluoropropene, HF and HCl;
  i') treating the stream D to give a stream D1 comprising 1-chloro-3,3,3-trifluoropropene, HCl and HF and a stream D2 comprising at least 50% by weight of HF;
  ii') recovering hydrochloric acid from the stream D1 to form a stream D3 of HCl and a stream D4 comprising 1-chloro-3,3,3-trifluoropropene, HCl and HF;
  iii') separating the stream D4 obtained in step ii') to form a stream D5 comprising at least 90% by weight and a stream D6 comprising 1-chloro-3,3,3-trifluoropropene, HCl and HF;
  iv') washing of said stream D6 obtained in step iii') with water to form a stream D7 comprising 1-chloro-3,3,3-trifluoropropene and an acidic aqueous solution D8;
  ii) carrying out the neutralization process according to the present invention starting from the stream D7 obtained in step iv') to form the gas stream C.

The present production process can also comprise a step iii) subsequent to step ii). Preferably, step iii) consists in drying said gas stream C comprising 1-chloro-3,3,3-trifluoropropene to form a dried stream C2 comprising 1-chloro-3,3,3-trifluoropropene. The drying step can be carried out using a molecular sieve, zeolite, inorganic salts such as calcium sulfate or calcium chloride, silica gel, activated carbon. Examples of molecular sieves and of zeolites are described in document WO 2017/050686. Examples of inorganic salts, of molecular sieves, of silica gel and of activated carbon are also described in WO 2017/031406. Examples of molecular sieves, of activated carbon and of silica gel are also described in WO 2016/148957. Preferably, the drying step will be carried out using a molecular sieve, in particular using a 3 A molecular sieve.

The present production process can also comprise a step iv) subsequent to step iii). Preferably, step iv) comprises one or more steps of distilling said stream C2 obtained in step iii).

Thus according to one particular embodiment, said process for producing 1-chloro-3,3,3-trifluoropropene according to the present invention comprises the steps of:
  i) bringing the hydrofluoric acid (HF) into contact, in a reactor, with a starting composition comprising at least one chlorinated compound selected from the group consisting of 1,1,3,3-tetrachloropropene, 1,3,3,3-tetrachloropropene and a mixture of the two, to obtain a stream D comprising 1-chloro-3,3,3-trifluoropropene, HF and HCl;
  i') treating the stream D to give a stream D1 comprising 1-chloro-3,3,3-trifluoropropene, HCl and HF and a stream D2 comprising at least 50% by weight of HF;
  ii') recovering hydrochloric acid from the stream D1 to form a stream D3 of HCl and a stream D4 comprising 1-chloro-3,3,3-trifluoropropene, HCl and HF;
  iii') separating the stream D4 obtained in step ii') to form a stream D5 comprising at least 90% by weight and a stream D6 comprising 1-chloro-3,3,3-trifluoropropene, HCl and HF;

iv') washing of said stream D6 obtained in step iii') with water to form a stream D7 comprising 1-chloro-3,3,3-trifluoropropene and an acidic aqueous solution D8;
ii) carrying out the neutralization process according to the present invention starting from the stream D7 obtained in step iv') to form the gas stream C;
iii) drying of said gas stream C comprising 1-chloro-3,3,3-trifluoropropene to form a dried stream C2 comprising 1-chloro-3,3,3-trifluoropropene; and
iv) distilling said stream C2 using one or more distillation columns to form a stream C3 comprising 1-chloro-3,3,3-trifluoropropene.

Preferably, said production process according to the present invention is carried out continuously.

According to another aspect of the present invention, a composition is provided. Said composition comprises 1-chloro-3,3,3-trifluoropropene and 1-chloro-1,3,3-trifluoropropene. Preferably, the molar content of 1-chloro-1,3,3-trifluoropropene is less than 110 ppm in said composition. Preferably, the molar content of 1-chloro-3,3,3-trifluoropropene in said composition is greater than 85%. Preferably, in said composition, 1-chloro-3,3,3-trifluoropropene represents at least 90 mol % of trans-1-chloro-3,3,3-trifluoropropene, more particularly at least 92 mol % of trans-1-chloro-3,3,3-trifluoropropene, preferably at least 95 mol % of trans-1-chloro-3,3,3-trifluoropropene, more preferably at least 98 mol % of trans-1-chloro-3,3,3-trifluoropropene; the remainder being represented by cis-1-chloro-3,3,3-trifluoropropene. Preferably, in said composition, 1-chloro-3,3,3-trifluoropropene is trans-1-chloro-3,3,3-trifluoropropene.

Thus, advantageously, said composition comprises a molar content of 1-chloro-3,3,3-trifluoropropene of greater than 87% and a molar content of 1-chloro-1,3,3-trifluoropropene of less than 110 ppm, advantageously less than 100 ppm, preferably less than 90 ppm, more preferentially less than 80 ppm, in particular less than 70 ppm, more particularly less than 60 ppm, preferably less than 50 ppm. Preferably, in said composition, 1-chloro-3,3,3-trifluoropropene represents at least 90 mol % of trans-1-chloro-3,3,3-trifluoropropene, more particularly at least 92 mol % of trans-1-chloro-3,3,3-trifluoropropene, preferably at least 95 mol % of trans-1-chloro-3,3,3-trifluoropropene, more preferably at least 98 mol % of trans-1-chloro-3,3,3-trifluoropropene; the remainder being represented by cis-1-chloro-3,3,3-trifluoropropene. Preferably, in said composition, 1-chloro-3,3,3-trifluoropropene is trans-1-chloro-3,3,3-trifluoropropene.

Preferably, said composition comprises a molar content of 1-chloro-3,3,3-trifluoropropene of greater than 90% and a molar content of 1-chloro-1,3,3-trifluoropropene of less than 110 ppm, advantageously less than 100 ppm, preferably less than 90 ppm, more preferentially less than 80 ppm, in particular less than 70 ppm, more particularly less than 60 ppm, preferably less than 50 ppm. Preferably, in said composition, 1-chloro-3,3,3-trifluoropropene represents at least 90 mol % of trans-1-chloro-3,3,3-trifluoropropene, more particularly at least 92 mol % of trans-1-chloro-3,3,3-trifluoropropene, preferably at least 95 mol % of trans-1-chloro-3,3,3-trifluoropropene, more preferably at least 98 mol % of trans-1-chloro-3,3,3-trifluoropropene; the remainder being represented by cis-1-chloro-3,3,3-trifluoropropene. Preferably, in said composition, 1-chloro-3,3,3-trifluoropropene is trans-1-chloro-3,3,3-trifluoropropene.

More preferentially, said composition comprises a molar content of 1-chloro-3,3,3-trifluoropropene of greater than 92% and a molar content of 1-chloro-1,3,3-trifluoropropene of less than 110 ppm, advantageously less than 100 ppm, preferably less than 90 ppm, more preferentially less than 80 ppm, in particular less than 70 ppm, more particularly less than 60 ppm, preferably less than 50 ppm. Preferably, in said composition, 1-chloro-3,3,3-trifluoropropene represents at least 90 mol % of trans-1-chloro-3,3,3-trifluoropropene, more particularly at least 92 mol % of trans-1-chloro-3,3,3-trifluoropropene, preferably at least 95 mol % of trans-1-chloro-3,3,3-trifluoropropene, more preferably at least 98 mol % of trans-1-chloro-3,3,3-trifluoropropene; the remainder being represented by cis-1-chloro-3,3,3-trifluoropropene. Preferably, in said composition, 1-chloro-3,3,3-trifluoropropene is trans-1-chloro-3,3,3-trifluoropropene.

In particular, said composition comprises a molar content of 1-chloro-3,3,3-trifluoropropene of greater than 95% and a molar content of 1-chloro-1,3,3-trifluoropropene of less than 110 ppm, advantageously less than 100 ppm, preferably less than 90 ppm, more preferentially less than 80 ppm, in particular less than 70 ppm, more particularly less than 60 ppm, preferably less than 50 ppm. Preferably, in said composition, 1-chloro-3,3,3-trifluoropropene represents at least 90 mol % of trans-1-chloro-3,3,3-trifluoropropene, more particularly at least 92 mol % of trans-1-chloro-3,3,3-trifluoropropene, preferably at least 95 mol % of trans-1-chloro-3,3,3-trifluoropropene, more preferably at least 98 mol % of trans-1-chloro-3,3,3-trifluoropropene; the remainder being represented by cis-1-chloro-3,3,3-trifluoropropene. Preferably, in said composition, 1-chloro-3,3,3-trifluoropropene is trans-1-chloro-3,3,3-trifluoropropene.

More particularly, said composition comprises a molar content of 1-chloro-3,3,3-trifluoropropene of greater than 97% and a molar content of 1-chloro-1,3,3-trifluoropropene of less than 110 ppm, advantageously less than 100 ppm, preferably less than 90 ppm, more preferentially less than 80 ppm, in particular less than 70 ppm, more particularly less than 60 ppm, preferably less than 50 ppm. Preferably, in said composition, 1-chloro-3,3,3-trifluoropropene represents at least 90 mol % of trans-1-chloro-3,3,3-trifluoropropene, more particularly at least 92 mol % of trans-1-chloro-3,3,3-trifluoropropene, preferably at least 95 mol % of trans-1-chloro-3,3,3-trifluoropropene, more preferably at least 98 mol % of trans-1-chloro-3,3,3-trifluoropropene; the remainder being represented by cis-1-chloro-3,3,3-trifluoropropene. Preferably, in said composition, 1-chloro-3,3,3-trifluoropropene is trans-1-chloro-3,3,3-trifluoropropene.

Preferably, said composition comprises a molar content of 1-chloro-3,3,3-trifluoropropene of greater than 99% and a molar content of 1-chloro-1,3,3-trifluoropropene of less than 110 ppm, advantageously less than 100 ppm, preferably less than 90 ppm, more preferentially less than 80 ppm, in particular less than 70 ppm, more particularly less than 60 ppm, preferably less than 50 ppm. Preferably, in said composition, 1-chloro-3,3,3-trifluoropropene represents at least 90 mol % of trans-1-chloro-3,3,3-trifluoropropene, more particularly at least 92 mol % of trans-1-chloro-3,3,3-trifluoropropene, preferably at least 95 mol % of trans-1-chloro-3,3,3-trifluoropropene, more preferably at least 98 mol % of trans-1-chloro-3,3,3-trifluoropropene; the remainder being represented by cis-1-chloro-3,3,3-trifluoropropene. Preferably, in said composition, 1-chloro-3,3,3-trifluoropropene is trans-1-chloro-3,3,3-trifluoropropene.

Said composition can also comprise 1,1-dichloro-1,3,3-trifluoropropane. The molar content of 1,1-dichloro-1,3,3-trifluoropropane in said composition is between 10 and 200 ppm, preferably between 20 and 150 ppm, in particular between 50 and 100 ppm.

Thus, said composition may comprise a molar content of 1-chloro-3,3,3-trifluoropropene of greater than 85% and a molar content of 1-chloro-1,3,3-trifluoropropene of less than or equal to 110 ppm, advantageously less than or equal to 100 ppm, preferably less than or equal to 90 ppm, more preferentially less than 80 ppm, in particular less than 70 ppm, more particularly less than or equal to 60 ppm, preferably less than or equal to 50 ppm; and a molar content of 1,1-dichloro-1,3,3-trifluoropropane of between 10 and 200 ppm, preferably between 20 and 150 ppm, in particular between 50 and 100 ppm. Preferably, in said composition, 1-chloro-3,3,3-trifluoropropene represents at least 90 mol % of trans-1-chloro-3,3,3-trifluoropropene, more particularly at least 92 mol % of trans-1-chloro-3,3,3-trifluoropropene, preferably at least 95 mol % of trans-1-chloro-3,3,3-trifluoropropene, more preferably at least 98 mol % of trans-1-chloro-3,3,3-trifluoropropene; the remainder being represented by cis-1-chloro-3,3,3-trifluoropropene. Preferably, in said composition, 1-chloro-3,3,3-trifluoropropene is trans-1-chloro-3,3,3-trifluoropropene.

Advantageously, said composition may comprise a molar content of 1-chloro-3,3,3-trifluoropropene of greater than 87% and a molar content of 1-chloro-1,3,3-trifluoropropene of less than or equal to 110 ppm, advantageously less than or equal to 100 ppm, preferably less than or equal to 90 ppm, more preferentially less than or equal to 80 ppm, in particular less than or equal to 70 ppm, more particularly less than or equal to 60 ppm, preferably less than or equal to 50 ppm; and a molar content of 1,1-dichloro-1,3,3-trifluoropropane of between 10 and 200 ppm, preferably between 20 and 150 ppm, in particular between 50 and 100 ppm. Preferably, in said composition, 1-chloro-3,3,3-trifluoropropene represents at least 90 mol % of trans-1-chloro-3,3,3-trifluoropropene, more particularly at least 92 mol % of trans-1-chloro-3,3,3-trifluoropropene, preferably at least 95 mol % of trans-1-chloro-3,3,3-trifluoropropene, more preferably at least 98 mol % of trans-1-chloro-3,3,3-trifluoropropene; the remainder being represented by cis-1-chloro-3,3,3-trifluoropropene. Preferably, in said composition, 1-chloro-3,3,3-trifluoropropene is trans-1-chloro-3,3,3-trifluoropropene.

Preferably, said composition may comprise a molar content of 1-chloro-3,3,3-trifluoropropene of greater than 90% and a molar content of 1-chloro-1,3,3-trifluoropropene of less than or equal to 110 ppm, advantageously less than or equal to 100 ppm, preferably less than or equal to 90 ppm, more preferentially less than or equal to 80 ppm, in particular less than or equal to 70 ppm, more particularly less than or equal to 60 ppm, preferably less than or equal to 50 ppm; and a molar content of 1,1-dichloro-1,3,3-trifluoropropane of between 10 and 200 ppm, preferably between 20 and 150 ppm, in particular between 50 and 100 ppm. Preferably, in said composition, 1-chloro-3,3,3-trifluoropropene represents at least 90 mol % of trans-1-chloro-3,3,3-trifluoropropene, more particularly at least 92 mol % of trans-1-chloro-3,3,3-trifluoropropene, preferably at least 95 mol % of trans-1-chloro-3,3,3-trifluoropropene, more preferably at least 98 mol % of trans-1-chloro-3,3,3-trifluoropropene; the remainder being represented by cis-1-chloro-3,3,3-trifluoropropene. Preferably, in said composition, 1-chloro-3,3,3-trifluoropropene is trans-1-chloro-3,3,3-trifluoropropene.

More preferentially, said composition may comprise a molar content of 1-chloro-3,3,3-trifluoropropene of greater than 92% and a molar content of 1-chloro-1,3,3-trifluoropropene of less than or equal to 110 ppm, advantageously less than or equal to 100 ppm, preferably less than or equal to 90 ppm, more preferentially less than or equal to 80 ppm, in particular less than or equal to 70 ppm, more particularly less than or equal to 60 ppm, preferably less than or equal to 50 ppm; and a molar content of 1,1-dichloro-1,3,3-trifluoropropane of between 10 and 200 ppm, preferably between 20 and 150 ppm, in particular between 50 and 100 ppm. Preferably, in said composition, 1-chloro-3,3,3-trifluoropropene represents at least 90 mol % of trans-1-chloro-3,3,3-trifluoropropene, more particularly at least 92 mol % of trans-1-chloro-3,3,3-trifluoropropene, preferably at least 95 mol % of trans-1-chloro-3,3,3-trifluoropropene, more preferably at least 98 mol % of trans-1-chloro-3,3,3-trifluoropropene; the remainder being represented by cis-1-chloro-3,3,3-trifluoropropene. Preferably, in said composition, 1-chloro-3,3,3-trifluoropropene is trans-1-chloro-3,3,3-trifluoropropene.

In particular, said composition may comprise a molar content of 1-chloro-3,3,3-trifluoropropene of greater than 95% and a molar content of 1-chloro-1,3,3-trifluoropropene of less than or equal to 110 ppm, advantageously less than or equal to 100 ppm, preferably less than or equal to 90 ppm, more preferentially less than or equal to 80 ppm, in particular less than or equal to 70 ppm, more particularly less than or equal to 60 ppm, preferably less than or equal to 50 ppm; and a molar content of 1,1-dichloro-1,3,3-trifluoropropane of between 10 and 200 ppm, preferably between 20 and 150 ppm, in particular between 50 and 100 ppm. Preferably, in said composition, 1-chloro-3,3,3-trifluoropropene represents at least 90 mol % of trans-1-chloro-3,3,3-trifluoropropene, more particularly at least 92 mol % of trans-1-chloro-3,3,3-trifluoropropene, preferably at least 95 mol % of trans-1-chloro-3,3,3-trifluoropropene, more preferably at least 98 mol % of trans-1-chloro-3,3,3-trifluoropropene; the remainder being represented by cis-1-chloro-3,3,3-trifluoropropene. Preferably, in said composition, 1-chloro-3,3,3-trifluoropropene is trans-1-chloro-3,3,3-trifluoropropene.

More particularly, said composition may comprise a molar content of 1-chloro-3,3,3-trifluoropropene of greater than 97% and a molar content of 1-chloro-1,3,3-trifluoropropene of less than or equal to 110 ppm, advantageously less than or equal to 100 ppm, preferably less than or equal to 90 ppm, more preferentially less than or equal to 80 ppm, in particular less than or equal to 70 ppm, more particularly less than or equal to 60 ppm, preferably less than or equal to 50 ppm; and a molar content of 1,1-dichloro-1,3,3-trifluoropropane of between 10 and 200 ppm, preferably between 20 and 150 ppm, in particular between 50 and 100 ppm. Preferably, in said composition, 1-chloro-3,3,3-trifluoropropene represents at least 90 mol % of trans-1-chloro-3,3,3-trifluoropropene, more particularly at least 92 mol % of trans-1-chloro-3,3,3-trifluoropropene, preferably at least 95 mol % of trans-1-chloro-3,3,3-trifluoropropene, more preferably at least 98 mol % of trans-1-chloro-3,3,3-trifluoropropene; the remainder being represented by cis-1-chloro-3,3,3-trifluoropropene. Preferably, in said composition, 1-chloro-3,3,3-trifluoropropene is trans-1-chloro-3,3,3-trifluoropropene.

Preferably, said composition may comprise a molar content of 1-chloro-3,3,3-trifluoropropene of greater than 99% and a molar content of 1-chloro-1,3,3-trifluoropropene of less than or equal to 110 ppm, advantageously less than or equal to 100 ppm, preferably less than or equal to 90 ppm, more preferentially less than or equal to 80 ppm, in particular less than or equal to 70 ppm, more particularly less than or equal to 60 ppm, preferably less than or equal to 50 ppm; and a molar content of 1,1-dichloro-1,3,3-trifluoropropane of between 10 and 200 ppm, preferably between 20 and 150 ppm, in particular between 50 and 100 ppm. Preferably, in said composition, 1-chloro-3,3,3-trifluoropropene represents at least 90 mol % of trans-1-chloro-3,3,3-trifluoropropene, more particularly at least 92 mol % of trans-1-chloro-3,3,3-trifluoropropene, preferably at least 95 mol % of trans-1-chloro-3,3,3-trifluoropropene, more preferably at least 98 mol % of trans-1-chloro-3,3,3-trifluoropropene; the remainder being represented by cis-1-chloro-3,3,3-trifluoropropene. Preferably, in said composition, 1-chloro-3,3,3-trifluoropropene is trans-1-chloro-3,3,3-trifluoropropene.

EXAMPLES

The examples are carried out in a reactor surmounted by a scrubbing column (both being heat insulated). The scrubbing column (internal diameter=24 mm, height=300 mm) is packed with Raschig rings (internal diameter=3 mm, external diameter=5 mm, length=5 mm, fraction of life in the packed column=63%). A basic solution was introduced and was turned in circles through a scrubbing column packed with Raschig rings (about 185 ml/min). The basic solution is brought to a temperature of 30° C. or 50° C. according to the examples. A composition comprising 95.8 mol % of trans-1-chloro-3,3,3-trifluoropropene, 2.4 mol % of cis-1-chloro-3,3,3-trifluoropropene (i.e. a trans/cis molar ratio of 39.9), approximately 120 ppm of 1,1-dichloro-1,3,3-trifluoropropane and approximately 25 ppm of 1-chloro-1,3,3-trifluoropropene was then introduced into the reactor at a flow rate of 5 g/h. The contents of the constituents of the composition are expressed in moles. Said composition can be obtained by carrying out the process for producing 1-chloro-3,3,3-trifluoropropene as described in the present application. The gas stream was collected in order to be be dried over anhydrous $CaCl_2$ and trapped using a liquid nitrogen trap. The gas stream was analyzed by gas chromatography. The amount of 1-chloro-1,3,3-trifluoropropene is determined after neutralization.

The basic solutions tested (content expressed by weight) and the results are given below in table 1.

TABLE 1

| Example | Basic solution | T (° C.) | HCFO-1233zb content |
| --- | --- | --- | --- |
| Example 1 (Comp.) | 5% KOH | 30° C. | 130 ppm |
| Example 2 (Inv.) | 5% NaOH | 30° C. | 100 ppm |
| Example 3 (Comp.) | 20% KOH | 50° C. | 120 ppm |
| Example 4 (Inv.) | 20% NaOH | 50° C. | 50 ppm |

As demonstrated by the examples above, the use of a basic NaOH solution makes it possible to limit the formation of 1-chloro-1,3,3-trifluoropropene during the neutralization step; the HCFC-243fc content being slightly reduced. The use of a basic KOH solution results in a higher content of HCFO-1233zb and a large decrease in the content of HCFC-243fc. The trans-1-chloro-3,3,3-trifluoropropene thus obtained comprises less HCFO-1233zb capable of disrupting its effectiveness in the various fields of application. In addition, it is easier to separate 1,1-dichloro-1,3,3-trifluoropropane from trans-1-chloro-3,3,3-trifluoropropene than to separate 1-chloro-1,3,3-trifluoropropene from trans-1-chloro-3,3,3-trifluoropropene. The present process therefore represents a considerable advantage in a process for producing and purifying trans-1-chloro-3,3,3-trifluoropropene.

The invention claimed is:

1. A process for neutralizing a composition A comprising 1-chloro-3,3,3-trifluoropropene, 1,1-dichloro-1,3,3-trifluoropropane and one or more acid compound(s) of formula HX with X=F or Cl; said process comprising the step a) of bringing said composition A into contact with a solution B under conditions capable of limiting the formation of 1-chloro-1,3,3-trifluoropropene, wherein solution B is a NaOH solution with a weight content of NaOH of from 5 to 40% by weight.

2. The process as claimed in claim 1, wherein said conditions capable of limiting the formation of 1-chloro-1,3,3-trifluoropropene comprise implementing step a) with a basic solution B.

3. The process as claimed in claim 1, wherein said solution B of step a) is an aqueous solution.

4. The process as claimed in claim 1, wherein step a) is carried out at a temperature of 10° C. to 90° C.

5. The process as claimed in claim 1, wherein step a) is carried out with a residence time of between 1 second and 5 minutes.

6. The process as claimed in claim 1, wherein the 1-chloro-3,3,3-trifluoropropene is in the trans form.

7. The process as claimed in claim 1, wherein step a) makes it possible to obtain a gas stream C comprising 1-chloro-3,3,3-trifluoropropene, 1-chloro-1,3,3-trifluoropropene and 1,1-dichloro-1,3,3-trifluoropropane.

8. The process as claimed in claim 1, wherein the 1-chloro-1,3,3-trifluoropropene is obtained by dehydrochlorination of 1,1-dichloro-1,3,3-trifluoropropane.

9. A process for producing 1-chloro-3,3,3-trifluoropropene comprising the steps of:
   i. bringing hydrofluoric acid (HF) into contact, in a reactor, with a starting composition comprising at least one chlorinated compound selected from the group consisting of 1,1,3,3-tetrachloropropene, 1,3,3,3-tetrachloropropene and a mixture of the two, under conditions sufficient to obtain a stream D comprising 1-chloro-3,3,3-trifluoropropene, 1,1-dichloro-1,3,3-trifluoropropane, HF and/or HCl;
   ii. carrying out the process as claimed in claim 1 using the stream D obtained in step i).

10. A composition comprising 1-chloro-3,3,3-trifluoropropene and 1-chloro-1,3,3-trifluoropropene, the molar content of 1-chloro-1,3,3-trifluoropropene being less than 110 ppm in said composition, wherein the molar content of 1-chloro-3,3,3-trifluoropropene in said composition is greater than 90%.

11. The composition as claimed in claim 10, wherein the molar content of 1-chloro-1,3,3-trifluoropropene is less than 100 ppm.

12. The composition as claimed in claim 10, wherein the composition further comprises 1,1-dichloro-1,3,3-trifluoropropane.

13. A process for preparing 1-chloro-1,3,3-trifluoropropene by dehydrochlorination of 1,1-dichloro-1,3,3-trifluoropropane in the presence of a NaOH solution with a weight content of NaOH of from 5 to 40% by weight.

14. The process as claimed in claim 13, wherein the process is carried out at a temperature between 10° C. and 150° C.

* * * * *